United States Patent [19]
Schenck

[11] Patent Number: 5,493,999
[45] Date of Patent: Feb. 27, 1996

[54] BUTTERFLY FEEDER

[75] Inventor: Marc W. Schenck, Middletown, R.I.

[73] Assignee: Woodkarter Kits, Inc., Yarmouth, Me.

[21] Appl. No.: 348,489

[22] Filed: Dec. 2, 1994

[51] Int. Cl.⁶ .................................................. A01K 7/00
[52] U.S. Cl. ............................................................ 119/72
[58] Field of Search ............................ 119/72, 77, 61, 119/57.8, 57.9, 52.2, 52.3

[56] References Cited

U.S. PATENT DOCUMENTS

| | | |
|---|---|---|
| 3,301,220 | 1/1967 | Wueen ........................................ 119/77 |
| 4,691,665 | 9/1987 | Hefner ........................................ 119/77 |
| 5,062,390 | 11/1991 | Beacherer .................................. 119/72 |
| 5,222,990 | 6/1993 | Elliott .................................... 119/61 X |
| 5,269,258 | 12/1993 | Brown . | |
| 5,303,674 | 4/1994 | Hyde, Jr. ................................... 119/77 |

Primary Examiner—Thomas Price
Attorney, Agent, or Firm—William B. Ritchie

[57] ABSTRACT

A butterfly feeder feeds a wide variety of butterfly species by presenting a variety of feeding choices. The butterfly feeder housing is formed with an upper surface over a reservoir of nectar or other butterfly feeding liquid. Wicks extend through the upper surface and are immersed at one end in the nectar for drawing nectar above the upper surface on the wicks for surface feeding by butterflies drinking nectar from the surface of the wicks. Elongate feeding tubes also extend from the upper surface into the reservoir and nectar for feeding by tube feeders with long tongues. Spikes are formed on the upper surface to hold fermenting fruit. Holes are provided for further feeding options. The butterfly feeder is constructed so that it is easily disassembled and reassembled for cleaning.

19 Claims, 3 Drawing Sheets

BUTTERFLY FEEDER

TECHNICAL FIELD

This invention relates to a new butterfly feeder for feeding a variety of butterfly species. The invention provides a wide choice of feeding opportunities according to the different feeding adaptions and habits of butterflies.

BACKGROUND ART

A variety of feeding adaptations and feeding habits have been identified in butterflies of North America. All butterflies feed on liquid, typically nectar produced by flowers. Butterflies have a proboscis or tongue in the form of a rolled up tube. For feeding, the tube is unrolled and nectar is forcibly drawn through the tube for drinking by the butterfly.

By way of example, larger butterflies such as the monarchs and swallowtails may have a proboscis or tongue up to 1½" (3.8 cm) long. The tongues of frittillaries may reach 2" (5.0 cm). These butterflies prefer to feed down the tapered "tube" of tubular shaped flowers.

On the other hand smaller butterflies such as buckeyes, checker spots, sulfurs, skippers, blues, and painted ladies have shorter tongues. These butterflies prefer surface feeding on nectar from the surface of nectar producing parts of the flower. Yet other butterflies including red admirals, question marks, morning cloaks, and angelwings are known to feed on the sweet liquid produced by fermenting fruit.

A butterfly feeder is described in the Brown U.S. Pat. No. 5,269,258. The Brown butterfly feeder is generally supported by hanging but can be mounted on a post. A cover is placed over a peripheral annular configuration feeding trough filled with a sugar solution which may contain other enumerated ingredients. Holes are formed in the cover for proboscis feeding by butterflies apparently inserting the tongue through a hole in the cover and into the sugar solution. The cover is also formed with depressions for receiving rotting fruit for fermenting juice feeders.

A disadvantage of the Brown butterfly feeder described in U.S. Pat. No. 5,269,258 is the limited choice of feeding opportunities available for butterflies. For example a long tongue feeding butterfly may not be attracted by the flat holes in the cover of the butterfly feeder. No choice and no opportunity is available for smaller butterflies that prefer surface feeding of nectar directly on flower parts. Furthermore, rotting fruit may fall out of the depressions in the cover during a wind.

OBJECTS OF THE INVENTION

It is therefore an object of the present invention to provide a butterfly feeder with a wide variety of feeding choices for attracting a wide variety of butterfly species. For example, an object of the invention is to provide a butterfly feeder that attracts surface feeders as well as tube feeders. A related object of the invention is to provide a suitable feeding environment for attracting tube feeders particularly long tongue butterflies. Overall the feeder presents colors and shapes attractive to butterflies.

Another object of the invention is to provide a butterfly feeder that also presents rotting fruit which generally can not be dislodged by the wind.

A further object of the invention is to provide a butterfly feeder with a housing of few parts that is easily disassembled and reassembled for cleaning etc.

DISCLOSURE OF THE INVENTION

In order to accomplish these results the present invention provides a butterfly feeder housing with an upper surface having colors and shapes attractive to a butterfly. For example the butterfly feeder housing may have the overall appearance of a flower displaying the colors yellow, red and white which are most attractive to butterflies. The housing is formed with a reservoir below the upper surface for storing butterfly feeding liquid such as nectar.

According to the invention at least one wick extends into the reservoir with one end of the wick immersed in the feeding liquid. The upper surface of the housing is formed with a wick hole and the wick extends through the wick hole. The other end of the wick therefore extends above the upper surface of the butterfly feeder housing. The wick draws feeding liquid from the reservoir above the upper surface for surface feeding by butterflies on feeding liquid on the surface of the wick.

In the preferred embodiment the butterfly feeder incorporates a plurality of wicks and the upper surface of the butterfly feeder housing is formed with a respective plurality of wick holes. The wicks extend above the upper surface of the housing for surface feeding and are self supporting. The wicks are preferably formed with a color of white or yellow for simulating flower stamens although other colors such as red can also be used.

An advantage of the wick structures is that they provide a feeding opportunity for butterflies that prefer surface feeding. These butterfly species are generally the smaller butterflies with a smaller tongue or proboscis adapted to feed on nectar on the surface of exposed flower parts.

According to the invention the butterfly feeder housing is also formed with a feeding tube or straw in the upper surface of the housing. The tube extends from the upper surface into the reservoir so that the lower end of the tube is immersed in the butterfly feeding liquid. In the preferred example the butterfly feeder housing is formed with a plurality of feeding tubes. The feeding tubes are also preferably tapered from a wider width at the upper surface to a narrower width in the reservoir for simulating a flower tube.

An advantage of the butterfly feeding tubes or straws is that they provide a feeding opportunity for butterflies that prefer to feed down an elongate tubular flower. Such butterflies are typically the larger butterflies with a long tongue or proboscis.

According to a further embodiment the butterfly feeder housing is formed with spikes or pegs on the upper surface projecting in an upward direction. The spikes are intended for holding rotting fruit for feeding butterflies that prefer drinking the sweet liquid formed by fermenting fruit. The spikes are generally spaced apart from the feeding wicks and tubes on the upper surface to avoid interference in the different feeding opportunities afforded by the new butterfly feeder. An advantage of the spikes or pegs is that they hold the fermenting fruit on the upper surface of the butterfly feeder housing even in a wind.

The butterfly feeder affords yet another feeding choice by forming a number of holes in the upper surface small enough to exclude bees, wasps and other flying insects. The holes are large enough to permit tongue feeding by butterflies. There are no tubes associated with these holes and so they are referred to herein as flat holes.

The butterfly feeder is assembled from only a few parts, for example four parts. The parts are designed for rapid disassembly and reassembly for cleaning etc.

DESCRIPTION OF PREFERRED EXAMPLE EMBODIMENTS AND BEST MODE OF THE INVENTION

Figure 1:
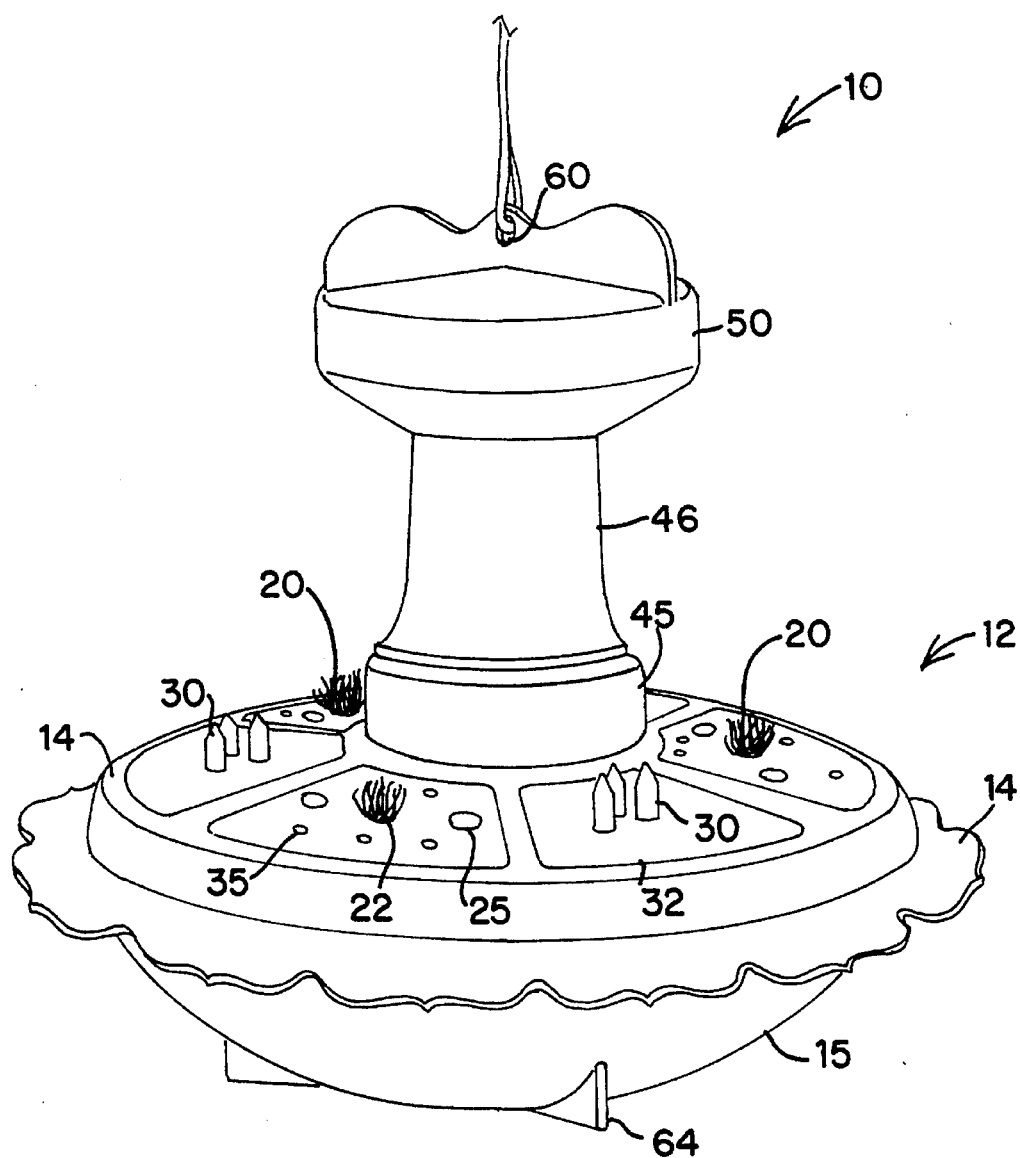
FIG. 1 is a perspective view of the butterfly feeder of the present invention.

A butterfly feeder 10 according to the present invention is illustrated in FIGS. 1–4. The butterfly feeder housing 12 includes an upper surface 14 which covers a reservoir 15. Butterfly feeding liquid, typically a nectar formula, is held in the bowl of the reservoir 15 where it is stored and available for a variety of butterfly feeding strategies hereafter described.

A first feeding strategy is provided by wicks 20 which have one end immersed in nectar inside the reservoir 15. The other end of the wicks extend through wick holes 22 formed in the upper surface 14 of the housing 12 a length for example about ¼ inch to ½ inch (0.6 cm–1.3 cm) above the upper surface 14. The ends of the wicks 20 are frayed above the upper surface 14 to simulate flower stamens and hold the wicks above the upper surface so they cannot slide back down the wick holes 22. Fraying of the ends of the wicks exposed above the upper surface cover 14 may occur naturally or the ends can be manually frayed and pulled apart to open approximately all of the end of the wick 20 above the upper surface 14 and expose the component threads.

The wicks are composed of any absorbent or adsorbent material capable of wicking action that are thick enough to be self supporting. Typical wick material is woven cotton. Color is preferably selected to be white or yellow, the natural color of most flower stamens for simulating flower parts. However it has been found that red wicks are also attractive to butterflies. Other colors may also be used.

A second feeding strategy is provided by tubes or straws 25 formed in the upper surface 14 and extending into the reservoir 15. The tubes are tapered from a greater width at the upper surface to, a narrower diameter at the lower end immersed in nectar. The taper simulates the appearance of a flower tube or channel such as provided, for example, by honeysuckle. The smaller end immersed in nectar also draws some nectar up into the tapered tube by capillary action further simulating a flower tube.

The feeding tubes 25 accessible through the upper surface 14 are in the range of ½" (1.2 cm) to 1" (2.5 cm) and typically ¾" (1.8 cm) in length. The feeding tubes 25 attract and provide a feeding opportunity for the larger butterflies with a longer proboscis and that prefer feeding down a flower tube or flower channel environment.

Figure 2:
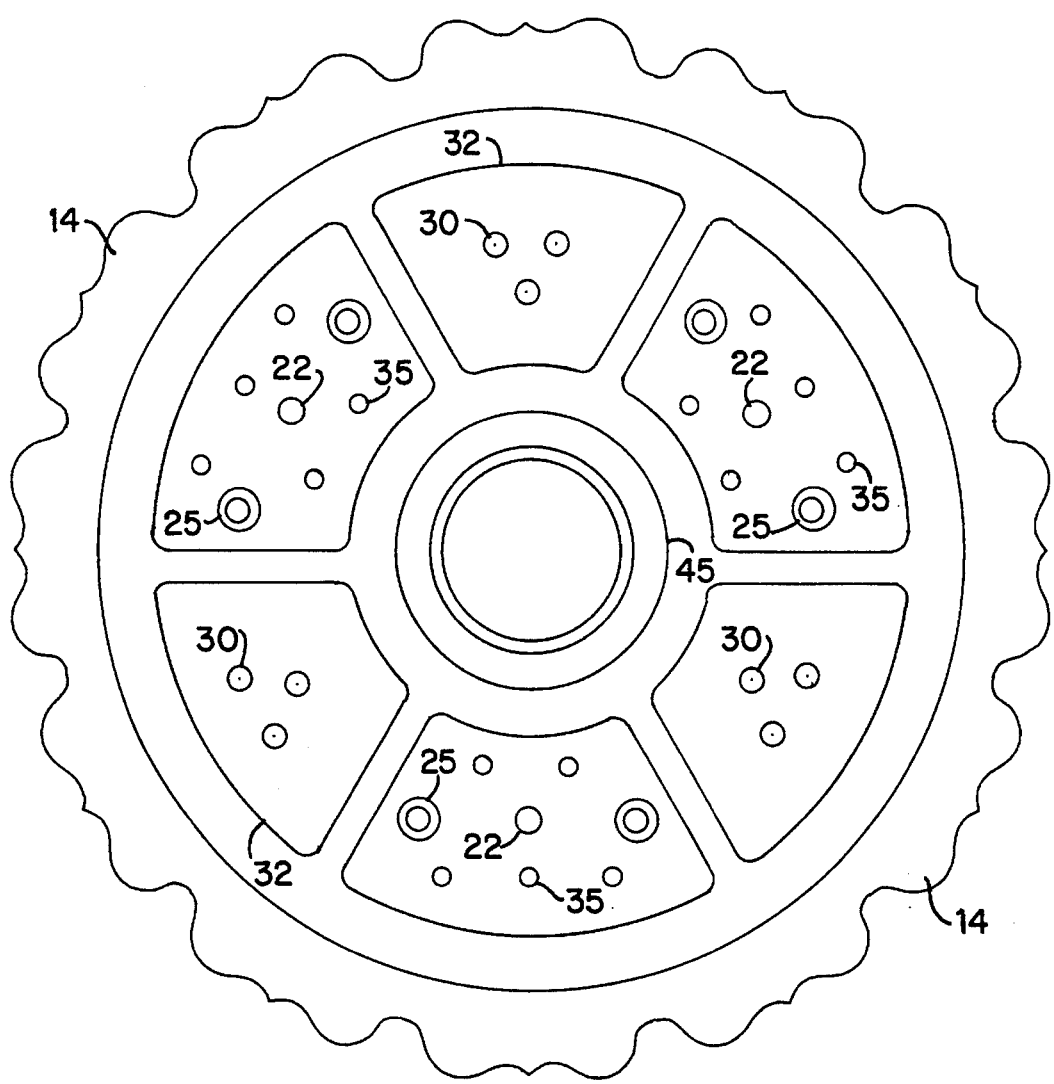
FIG. 2 is a plan view from above of the upper surface of the butterfly feeder housing with the hanging knob, collar and wicks removed.
Figure 3:
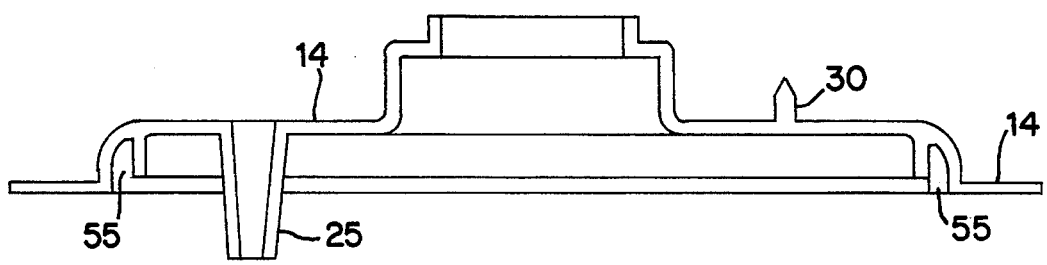
FIG. 3 is a side cross section view of the butterfly feeder housing through one of the tapered feeding tubes and also showing the reservoir and wicks.

Spikes or pegs 30 are formed on the upper surface projecting upward. The spikes 30 are assembled in groups of three at separate locations 32 spaced from the tubes 25 and wick holes 22 as shown in FIG. 2 to minimize interference between the different feeding opportunities. The spikes impale rotten fruit and hold the fermenting fruit for feeding by butterflies on the fermenting fruit liquid.

A final feeding opportunity is afforded by flat holes 35 formed in the upper surface and providing access to the reservoir of nectar below. The holes 35 are small enough to exclude flying insects but permit tongue feeding by butterflies through the holes. The holes 35 have no tubes or straws associated with them and so are referred to herein as flat holes.

Figure 4:
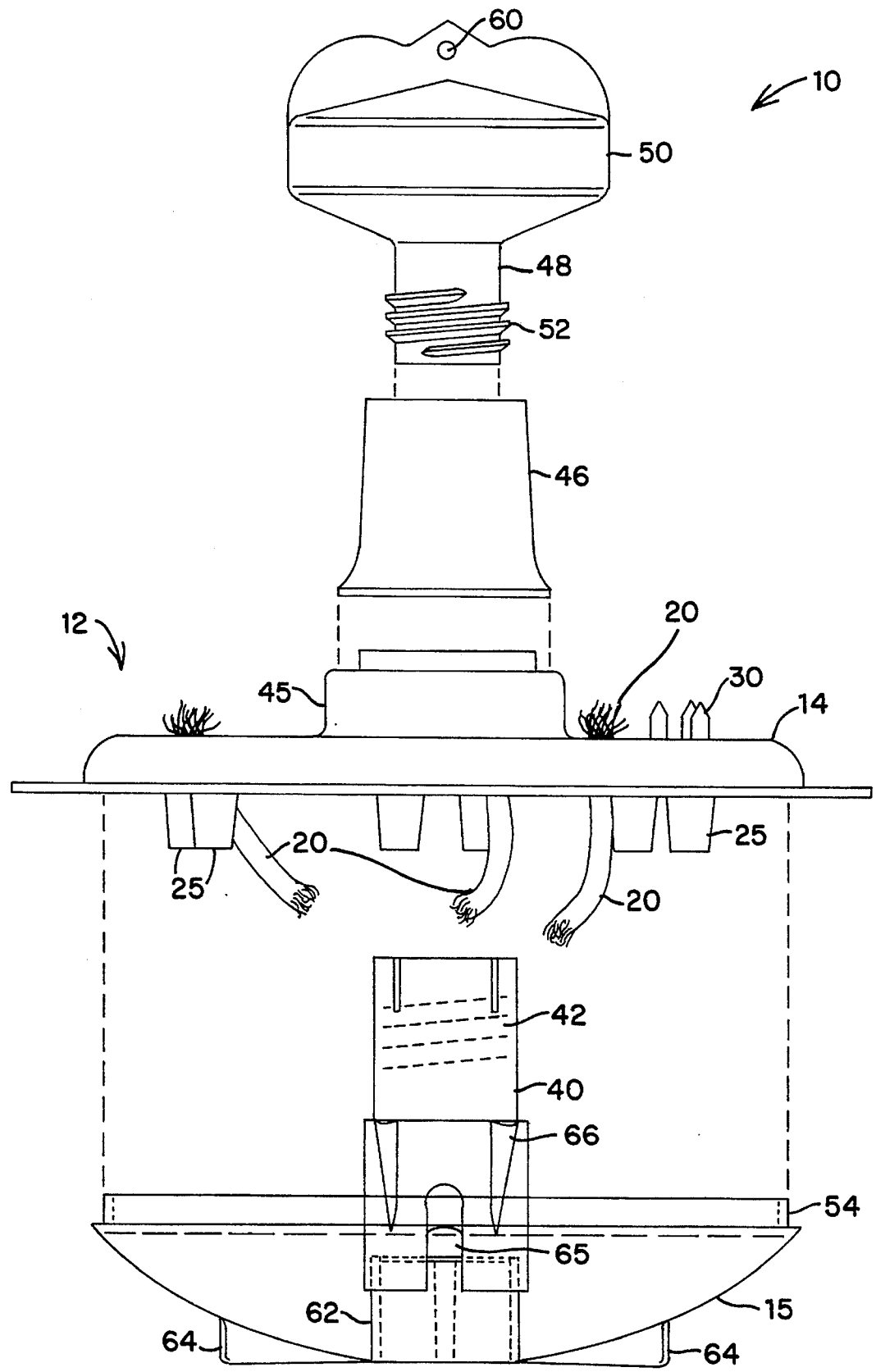
FIG. 4 is an exploded view of the parts of the feeder for rapid assembly and disassembly.

The construction of the butterfly feeder for ease in disassembling and reassembling for cleaning is illustrated in FIG. 4. The reservoir 15 is constructed with a central stem 40 with a threaded top 42. The cover 14 is formed with a central flange 45 through which reservoir stem 40 passes. A spacer collar 46 fits over the axial flange 45 of the cover and receives the complementary stem 48 of the hanging knob 50. The complementary stem 48 of hanging knob 50 is complementary to the reservoir stem 40 and includes a complementary threaded tip 52. The threaded tip 52 of the hanging handle or knob 50 engages the threaded end 42 of the reservoir stem 40.

A lip 54 formed around the perimeter of the reservoir 15 interfits with an annular slot 55 formed around the perimeter of the outer surface 14 as described in the Hyde U.S. Pat. No. 5,303,614. Shoulders 66 are also formed on the reservoir stem 40 and rest against the upper surface 14 around the central flange 45 for further support. The hanging handle stem 48 is then screwed into the reservoir stem 40 and the assembly is tightened together. The hanging knob 50 is formed with a hole 60 for hanging the butterfly feeder from an overhead support. The reservoir stem 40 is formed with a depression 62 below the reservoir bowl for alternatively mounting the feeder on a post. The reservoir 15 is also formed with legs 64 so that it can stand on a flat surface.

The reservoir 15 is normally filled with nectar to a fill line when the butterfly feeder is disassembled. The upper surface cover 14 is removed from the reservoir 15 and the reservoir 15 is placed on a flat surface where it is conveniently filled to the fill line. When the upper surface 14 and spacing collar 46 are assembled on the reservoir 15, the reservoir can alternatively be filled with nectar or other butterfly feeding liquid through the center of the reservoir stem 40. The reservoir stem 40 is formed with holes 65 that drain into the bowl of the reservoir 15. The reservoir 15 is typically constructed from transparent plastic for checking the level of the feeding liquid and determining whether refill is required as set forth in the Hyde U.S. Pat. No. 5,303,614.

A nectar formula suitable for butterfly feeding liquid typically includes sugars, salts, minerals and flavor attractants dissolved in water. The water to sugar ratio for a healthy feeding liquid is, for example, 20:1. Higher concentrations can be used up to, for example, 8:1 but the higher concentration may cause hardened abdomen syndrome in butterflies. A nectar formula containing dextrose, sucrose, fructose, sodium salts, orchacae extracts for flavor attractants, and minerals dissolved in boiling water can be obtained from Newport Butterfly Farm, 1151 Aquidneck Avenue, Middletown, R.I. 02842.

While the invention has been described with reference to particular example embodiments it is intended to cover all modifications and equivalents within the scope of the following claims.

I claim:

1. A butterfly feeder for feeding a variety of butterfly species comprising:

a butterfly feeder housing comprising an upper surface having colors and shapes attractive to butterflies;

said housing being formed with a reservoir below the upper surface for storing butterfly feeding liquid;

and at least one wick extending into the reservoir and having one end immersed in the feeding liquid;

said upper surface being formed with a wick hole with the wick extending through the hole so that the other end of the wick extends above the upper surface of the butterfly feeder housing for simulating nectar covered flower parts, for drawing feeding liquid from the reservoir above the upper surface and for surface feeding of butterflies on feeding liquid on said wick.

2. The butterfly feeder of claim 1 comprising a plurality of wicks and a plurality of wick holes formed in the upper surface as set forth in claim 1 thereby exposing a plurality of wick ends above the upper surface of the butterfly feeder.

3. The butterfly feeder of claim 2 wherein the wicks have a color selected from the group consisting of white, yellow, and red for simulating flower stamens.

4. The butterfly feeder of claim 1 wherein the butterfly feeder housing comprises an elongate feeding tube formed in the upper surface of the housing, said tube extending from the upper surface into the reservoir, said tube having the lower end immersed in the feeding liquid for tongue feeding by butterflies on the feeding liquid in the reservoir through the feeding tube.

5. The butterfly feeder of claim 4 comprising a plurality of feeding tubes formed in the upper surface.

6. The butterfly feeder of claim 4 wherein the feeding tube is tapered from a wider diameter at the upper surface to a narrower width in the reservoir to simulate a flower.

7. The butterfly feeder of claim 4 comprising spikes formed on the upper surface and projecting upward, said spikes being spaced from each other and being oriented generally parallel to each other for piercing and holding fermenting fruit for surface feeding by butterflies on the fermenting fruit liquid.

8. The butterfly feeder of claim 7 wherein the spikes are spaced from the wicks and feeding tubes so that the fermenting fruit does not interfere in the feeding strategies afforded by the wicks and feeding tubes.

9. The butterfly feeder of claim 4 wherein the upper surface is formed with flat holes to provide a further feeding opportunity for butterflies.

10. The butterfly feeder of claim 4 wherein the reservoir is constructed with a central reservoir stem and the upper surface is formed with a central hole and flange, said reservoir stem passing through the central hole and flange of the upper surface, and further comprising:

a spacing collar that fits over the reservoir stem and rests on the central flange of the outer surface;

and a hanging knob with a complementary stem that extends through the spacing collar and engages the reservoir stem for securing the parts together.

11. A butterfly feeder for feeding a variety of butterfly species comprising:

a butterfly feeder housing comprising an upper surface having colors and shapes attractive to butterflies;

said housing being formed with a reservoir below the upper surface for storing butterfly feeding liquid;

and at least one wick extending into the reservoir and having one end immersed in the feeding liquid;

said upper surface being formed with a wick hole with the wick extending through the hole so that the other end of the wick extends above the upper surface of the butterfly feeder housing for simulating nectar covered flower parts, for drawing feeding liquid from the reservoir above the upper surfaced and for surface feeding of butterflies on feeding liquid on said wick;

said butterfly feeder housing comprises an elongate feeding tube formed in the upper surface of the housing, said tube extending from the upper surface into the reservoir, said tube having the lower end immersed in the feeding liquid for tongue feeding by butterflies on the feeding liquid in the reservoir through the feeding tube.

12. The butterfly feeder of claim 11 comprising a plurality of wicks and a plurality of wick holes formed in the upper surface as set forth in claim 10 thereby exposing a plurality of wick ends above, the upper surface of the butterfly feeder housing, said butterfly feeder housing comprising a plurality of feeding tubes formed in the upper surface.

13. The butterfly feeder of claim 12 wherein the wicks have a color selected from the group consisting of white, yellow, and red for simulating flower stamens and wherein the feeding tube is tapered from a wider diameter at the upper surface to a narrower width in the reservoir to simulate a flower.

14. The butterfly feeder of claim 13 comprising spikes formed on the upper surface projecting upward, said spikes being spaced from each other and being oriented generally parallel to each other for piercing and holding fermenting fruit for surface feeding by butterflies on the fermenting fruit liquid and wherein the spikes are spaced from the wicks and feeding tubes so that the; fermenting fruit does not interfere in the feeding strategies afforded by the wicks and feeding tubes.

15. The butterfly feeder of claim 12 wherein the ends of the wicks extending above the upper surface 14 are frayed or opened to expose component threads of the wick.

16. The butterfly feeder of claim 11 wherein the upper surface is formed with flat holes to provide a further feeding opportunity for butterflies.

17. A butterfly feeder for feeding a variety of butterfly species comprising:

a butterfly feeder housing comprising an upper surface having colors and shapes attractive to butterflies;

said housing being formed with a reservoir below the upper surface for storing butterfly feeding liquid;

a plurality of wicks extending into the reservoir and having one end immersed in the feeding liquid;

said upper surface being formed with a respective plurality of wick holes with the wicks extending through the holes so that the other end of the wicks extends above the upper surface of the butterfly feeder housing for simulating nectar covered flower parts, for drawing feeding liquid from the reservoir above the upper surface, and for surface feeding of butterflies on feeding liquid on said wicks;

a plurality of elongate feeding tubes formed in the upper surface of the housing, said tubes extending from the upper surface into the reservoir, said tubes having the lower end immersed in the feeding liquid for tongue feeding by butterflies on the feeding liquid in the reservoir through the feeding tube;

spikes formed on the upper surface and projecting upward, said spikes being spaced from each other and being oriented generally parallel to each other for piercing and holding fermenting fruit for feeding by butterflies on the fermenting fruit liquid, said spikes being spaced from the wicks and feeding tubes so that the fermenting fruit does not interfere in the feeding strategies afforded by the wicks and feeding tubes;

said upper surface being formed with flat holes to provide a further feeding opportunity for butterflies.

18. The butterfly feeder of claim 17 wherein the reservoir is constructed with a central reservoir stem and the upper surface is formed with a central hole and flange, said reservoir stem passing through the central hole and flange of the upper surface, and further comprising:

a spacing collar that fits over the reservoir stem and rests on the central flange of the outer surface;

and a hanging knob with a complementary stem that extends through the spacing collar and engages the reservoir stem for securing the parts together.

19. The butterfly feeder of claim 17 wherein the ends of the wicks extending above the upper surface 14 are frayed or opened to expose component threads of the wick.

* * * * *